US010208291B2

(12) United States Patent
Buno et al.

(10) Patent No.: US 10,208,291 B2
(45) Date of Patent: Feb. 19, 2019

(54) METHOD FOR GENERATING HIGH-TITER HEPATITIS E VIRUS STOCKS AND TITRATION ASSAY FOR HEPATITIS E VIRUS

(71) Applicant: GRIFOLS, S.A., Barcelona (ES)

(72) Inventors: Brett Buno, Durham, NC (US); Terri Journigan, Wendell, NC (US); Joann Hotta, Raleigh, NC (US); Michael Burdick, Durham, NC (US)

(73) Assignee: GRIFOLS, S.A., Barcelona (ES)

( * ) Notice: Subject to any disclaimer, the term of this patent is extended or adjusted under 35 U.S.C. 154(b) by 85 days.

(21) Appl. No.: 15/213,766

(22) Filed: Jul. 19, 2016

(65) Prior Publication Data
US 2017/0022481 A1 Jan. 26, 2017

Related U.S. Application Data

(60) Provisional application No. 62/195,936, filed on Jul. 23, 2015.

(51) Int. Cl.
*C12N 7/00* (2006.01)
*C12Q 1/70* (2006.01)
*G01N 33/576* (2006.01)
*C12N 5/00* (2006.01)

(52) U.S. Cl.
CPC ............. *C12N 7/00* (2013.01); *C12N 5/0018* (2013.01); *C12Q 1/706* (2013.01); *C12Q 1/707* (2013.01); *G01N 33/576* (2013.01); *C12N 2501/05* (2013.01); *C12N 2770/28151* (2013.01)

(58) Field of Classification Search
None
See application file for complete search history.

(56) References Cited

U.S. PATENT DOCUMENTS

2013/0302790 A1 11/2013 Emerson et al.

FOREIGN PATENT DOCUMENTS

| WO | WO 2007/046962 A2 | 4/2007 |
| WO | WO 2007/046962 A3 | 4/2007 |
| WO | WO2007046962 | * 4/2007 |

OTHER PUBLICATIONS

Okamoto, J Gastroenterol (2013) vol. 48: pp. 147-158.*
Crameri, G., et al., Establishment, Immortalisation and Characterisation of Pteropid Bat Cell Lines, PLOS One, vol. 4, No. 12, Dec. 11, 2009.
Davis, H.E., et al., Polybrene increases retrovirus gene transfer efficiency by enhancing receptor-independent virus adsorption on target cell membranes, Biophysical Chemistry, vol. 97, No. 2-3, Jun. 19, 2002.
Extended European Search Report dated Nov. 25, 2016 in Application No. 16178844.3.
Tanaka, T., et al., Development and evaluation of an efficient cell-culture system for Hepatitis E virus, Journal of General Virology, vol. 88, No. 3, Mar. 1, 2007.
Vila-Brau, A., et al., Human HMGCS2 Regulates Mitochondrial Fatty Acid Oxidation and FGF21 Expression in HepG2 Cell Line, Journal of Biological Chemistry, vol. 286, No. 23, Apr. 18, 2011.

* cited by examiner

*Primary Examiner* — Shanon A. Foley
*Assistant Examiner* — Myron G Hill
(74) *Attorney, Agent, or Firm* — Knobbe, Martens, Olson & Bear, LLP

(57) ABSTRACT

Polybrene as an additive in cell culture medium is used in methods for the generation of high-titer hepatitis E virus stocks and assays for titration of hepatitis E virus. A cell culture medium containing polybrene is used for high-titer HEV generation, a method for determining the presence and/or the level of HEV in a sample, and an HEV titration assay using polybrene.

13 Claims, 9 Drawing Sheets

Specification includes a Sequence Listing.

METHOD FOR GENERATING HIGH-TITER HEPATITIS E VIRUS STOCKS AND TITRATION ASSAY FOR HEPATITIS E VIRUS

PRIORITY AND CROSS-REFERENCE TO RELATED APPLICATIONS

This application claims the benefit of priority to U.S. Provisional Application 62/195,936, filed on Jul. 23, 2015, which is hereby expressly incorporated by reference in its entirety.

REFERENCE TO SEQUENCE LISTING

The present application is being filed along with a Sequence Listing in electronic format. The Sequence Listing is provided as a file entitled DURC6_006AUS_SEQLIST.txt which is 1,093 bytes in size, created on Jul. 18, 2016 and last modified on Jul. 18, 2016. The information in the electronic format of the Sequence Listing is incorporated herein by reference in its entirety.

BACKGROUND

Field

The present invention refers to the field of virology, more precisely to methods for generating Hepatitis E Virus (hereinafter HEV) stocks. Specifically, the present invention discloses methods for propagating and titrating high titer HEV stocks.

Description of the Related Art

HEV (genus Hepevirus, family Hepeviridae) is a small non-enveloped/pseudo-enveloped virus, with a single-stranded positive-sense, polyadenylated RNA genome of approximately 7.2 kb. There are four genotypes of HEV that have been identified, but only one serotype. Genotypes 1 and 2 are mainly responsible for waterborne infections in underdeveloped countries and cause disease primarily in humans and higher primates. Infections are typically self-resolving and acute, lasting at most 2 to 7 weeks, but may be fatal especially in pregnant women. Genotypes 3 and 4 are associated with endemic (autochthonous) infections in industrialized countries. These two genotypes cause disease largely in swine but humans can become accidental hosts as a result of food or zoonotic exposure. Clinical disease is typically asymptomatic and mild in young adults, but can become clinically apparent in older men. In addition genotype 3 and 4 infections can become chronic in immune-suppressed persons, such as organ-transplant patients or AIDS patients.

Recently hepatitis E has been categorized as a transfusion transmittable infectious disease. Given the worldwide spread of HEV in recent years, concerns have been raised regarding the safety of blood- and plasma-derived products. The virus safety profile of blood- and plasma-derived products can be assured by performing clearance studies that demonstrate the virus reduction and/or clearance capacity of their manufacturing processes. During these clearance studies a known amount of virus is deliberately spiked into a blood or a plasma product intermediate and then the spiked material is processed using a bench scale model of the manufacturing process. Virus reduction and/or clearance across a step is determined by comparing the amount of virus before and after treatment.

Virus clearance studies require large quantities of high titer virus and the lack of an efficient cell culture system for HEV has hampered the ability to perform such studies for HEV. Several HEV cell culture systems have recently been developed to address this problem.

A genotype 3 and a genotype 4 strain were adapted by Okamoto and colleagues to grow in A549 human lung cells reaching HEV RNA titers of $3.9 \times 10^8$ copies/mL. In addition, said genotype 4 strain was also cultured in PLC/PRF/5 cells (human hepatoma cells) but with lower titers.

A second genotype 3 (strain Kernow-C1) was adapted by Emerson and colleagues to grow in HepG2/C3A human hepatoma cells obtaining a titer of $4.61 \times 10^8$ genomes/mL after 6 passages. Studies showed that the adaptation for growth in vitro resulted after the acquisition of 174 ribonucleotides of the S17 human ribosomal protein gene. Because genomes with the same insertion were detected in the original virus inoculum, a fecal suspension from a chronically infected HIV-1 patient, the recombination/insertion event had occurred naturally and was not an artifact of cell culture. Attempts to grow said strain in PLC/PRF/5 and A549 cells were unsuccessful or resulted in lower titers, but the virus infected and replicated in kidney cells from swine, the major zoonotic host for genotype 3 viruses.

Human hepatoma cells are difficult to grow and may require special cell plating methods including the use of coatings such as collagen, fibronectin, gelatin and/or poly-L-lysine to facilitate cell attachment and/or cell growth. In addition, not all of these coatings work well for all cell types.

SUMMARY

In some embodiments, a method of producing a high-titer of Hepatitis E Virus is provided, the method comprising: culturing a cell line in vitro in a medium comprising a concentration of polybrene, and infecting the cell line with HEV. In some embodiments of the method, the cell line used is HepG2 (ATCC number HB-8065) or HepG2/C3A (ATCC number CRL-10741). In some embodiments of the method, the concentration of polybrene is about 1 µg/ml-about 5 µg/ml. In some embodiments of the method, the high titer is about $10^8$ copies/mL-about $10^{10}$ copies/mL. In some embodiments of the method, the high titer is about $10^7$ copies/mL-about $10^{10}$ copies/mL. In some embodiments, the method further comprises the steps of adding a concentration of polybrene to the medium; a passaging the HEV-infected cell line in the medium comprising polybrene; and collecting the medium and/or infected cells. In some embodiments of the method, the concentration of polybrene is about 1 µg/ml-about 5 µg/ml. In some embodiments of the method, the high titer of HEV obtained in the medium and/or infected cells is about $10^8$ copies/mL-about $10^{10}$ copies/mL. In some embodiments of the method, the high titer of HEV obtained in the medium and/or infected cells is about $10^7$ copies/mL-about $10^{10}$ copies/mL.

In some embodiments, a method of determining a presence and/or a level of HEV in a sample is provided, the method comprising the steps of: providing the sample to a mixture comprising a cell line and a culture medium, wherein said culture medium comprises polybrene; incubating the mixture comprising the sample from the previous step to allow for the propagation of the HEV, if present in the sample; collecting a portion of the previous step, said portion comprising HEV, if present and propagated during the previous step; and measuring the presence and/or the level of a biological substance associated with HEV in the collected portion. In some embodiments of the method, the cell line is selected from the group consisting of cell lines of HepG2 (ATCC number HB-8065) and HepG2/C3A (ATCC number CRL-10741). In some embodiments of the method, said biological substance comprises a polynucleotide and/or a polypeptide sequence of HEV. In some embodiments of the method, said measuring comprises the steps of: providing a first reaction mixture by mixing the collected portion with a first solution so as to expose a polynucleotide of HEV, if HEV is present in the collected portion, wherein the polynucleotide is an RNA of HEV; providing a second reaction mixture by adding, to the first reaction mixture, a first reagent so as to produce a complementary deoxyribonucleic acid (cDNA) that is at least partially complementary to the RNA of HEV; providing a third reaction mixture by adding, to the second reaction mixture, a second reagent comprising a pair of polynucleotides to amplify a sequence of the cDNA that is at least partially complementary to each of the pair of polynucleotides; providing a fourth reaction mixture by amplifying the sequence; and determining a concentration of the amplified sequence in the fourth reaction mixture. In some embodiments of the method, said determining the concentration comprises: providing the fourth reaction mixture; providing a one or more controls comprising a predetermined amount of the cDNA of HEV; adding an agent to the fourth reaction mixture and the one or more controls, wherein said agent is at least partially specific to the amplified sequence in the fourth reaction mixture and the predetermined amount of the cDNA of HEV in the one or more controls; and calculating a level of recognition of HEV by the agent in the fourth reaction mixture relative to the one or more controls. In some embodiments of the method, said pair of polynucleotides comprises:

a)
(SEQ ID NO: 1)
5'-CGGCTATCGGCCAGAAGTT-3' b)
(SEQ ID NO: 2)
5'-CCGTGGCTATAACTGTGGTCT-3'

In some embodiments of the method, the agent comprises:

(SEQ ID NO: 3)
5'-FAM-TTTTTACGC-ZEN-AGGCTGCCAAGGCC-3IABkFQ-3'

In some embodiments, a culture medium for generating a high-titer HEV comprising polybrene in the range of about 1 µg/ml-about 5 µg/ml is provided. In some embodiments, the high-titer HEV is about $10^8$ copies/mL-about $10^{10}$ copies/mL. In some embodiments, the high-titer HEV is about $10^7$ copies/mL-about $10^{10}$ copies/mL.

In some embodiments, an HEV titration assay comprising the use of polybrene is provided. In some embodiments of the assay, the concentration of polybrene used is in the range of about 1 µg/ml-about 5 µg/ml.

BRIEF DESCRIPTION OF THE DRAWINGS

FIG. 1A shows HepG2/C3A cells cultured with DMEM+ 10% FBS+Non-essential amino acids, fungizone, HEPES, gentamicin (NHG).

FIG. 1B shows HepG2/C3A cells cultured with DMEM+ 10% FBS+NHG+pyruvate.

FIG. 1C shows HepG2/C3A cells cultured with DMEM+ 10% FBS+NHG+pyruvate+polybrene.

FIG. 2A shows HepG2/C3A cells cultured with DMEM+ 10% FBS+NHG.

FIG. 2B shows HepG2/C3A cells cultured with DMEM+ 10% FBS+NHG+pyruvate.

FIG. 2C shows HepG2/C3A cells cultured with DMEM+ 10% FBS+NHG+pyruvate+polybrene.

DETAILED DESCRIPTION

Figure 1A:
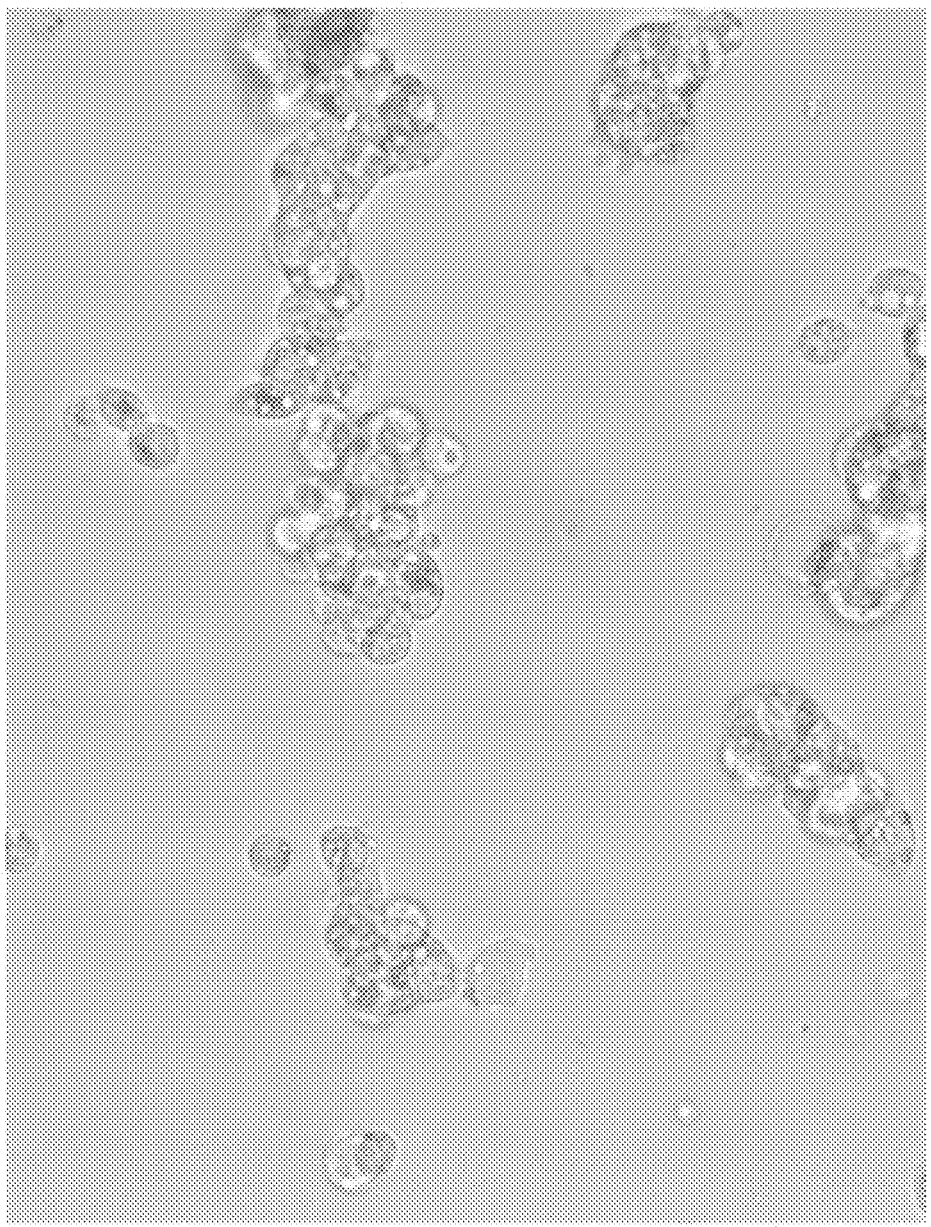
FIG. 1A-FIG. 1C show images taken at 20× magnification of HepG2/C3A cells cultured for 1 day with different cell culture media according to some embodiments of the disclosure herein.

The invention relates to a process for generating high-titer stocks of hepatitis E virus (HEV) suitable for use in virus clearance studies and a method for determining infectious HEV titers. The present invention comprises a simple method to propagate high titer HEV in cell culture for use in studies to evaluate the HEV clearance capacity of manufacturing processes of blood- and plasma-derived products.

As previously discussed, HEV has been adapted to grow in cell culture by Okamoto and colleagues, using PLC/PRF/5 human hepatoma cells and A549 human lung cells, and by Emerson and colleagues, using HepG2/C3A human hepatoma cells. Human hepatoma cells are difficult to grow and may require special cell plating methods. Emerson's laboratories coats plates with rat tail collagen I before seeding cells, while Okamoto's laboratories uses plates purchased from IWAKI, some of which are collagen-coated. Table 1 compares HEV titers from various cell culture systems and lists the methods used by different laboratories to enhance cell plating. Collagen and other coatings such as fibronectin, gelatin and poly-L-lysine facilitate cell attachment and/or cell growth so difficult-to-grow cells can reach higher densities and, thereby, yield high titer virus.

TABLE 1

Comparison of HEV Titers from Various Cell Culture Systems

| Lab | Cell plating enhancement method | Cells | HEV strain (genotype) | HEV Pass # | Log10 RNA copies/mL | Reference |
|---|---|---|---|---|---|---|
| Okamoto | IWAKI plates | PLC/PR F/5 & A549 | JE03-1760F (3) | 45 | 8-9 | Tanaka, et al. (2007) J Gen Virol 88: 903-911 |
|  |  |  | JE-JF5/15F (4) | 25 | 9-10 |  |
| Emerson | Rat Tail Collagen I coated plates | HepG2/ C3A | Kernow-C1 Passage 6 (3) | 6 | 8.7 | Patent Application US 2013 0302790 A1 |
| Grifols | Polybrene in media | HepG2/ C3A | Kernow-C1 Passage 6 (3) | 12 | 8.2 | Experiment VM1893 |
|  |  |  |  | 13 | 8.5 |  |
|  |  |  |  | 14 | 8.9 |  |
|  |  |  |  | 34 | 8.9 |  |
|  |  |  |  | 35 | 8.9 |  |
|  |  |  |  | 36 | 8.9 |  |

In some embodiments of the present invention, instead of using a coating such as collagen or other coatings to facilitate cell attachment and/or cell growth, a culture method for HEV involving the use of polybrene (also known as hexadimethrine bromide and 1,5-dimethyl-1,5-diazaundeca-methylene polymetho-bromide) is provided.

Polybrene is an inexpensive cationic polymer typically used in cell culture to increase the infection efficiency of retroviruses by decreasing the charge repulsion between virus and cells. The capacity of polybrene to bring different objects closer together is used in our invention to facilitate the attachment of human hepatoma cells to plating surfaces and HEV to cells. Polybrene is simply added to the cell culture media that is used for cell and virus propagation. The present invention obviates the need to purchase expensive plates pre-coated with collagen or other coating agents or to pre-coat plates with collagen or other coating agents before cell seeding and virus infection.

HEV usually replicates to low titers in vivo so growth in vitro is difficult. Methods for culturing HEV to yield high-titer stocks suitable for use in virus clearance studies were not previously available.

In one aspect of the invention disclosed herein, propagation of high titer HEV in cell culture is possible by using media supplemented with polybrene.

Polybrene is an inexpensive cationic polymer used in cell culture to increase the infection efficiency of retroviruses (enveloped viruses) by decreasing the charge repulsion between virus and cells. In some embodiments of the invention, polybrene is added to cell culture media to facilitate the attachment of HEV, a non-enveloped/pseudo-enveloped virus to cells. In addition, the presence of polybrene improves cell attachment and proliferation, thereby, enhancing the overall production of HEV in infected cells.

Therefore, in a first embodiment the present invention refers to a method of producing high-titer HEV in in vitro cultures based on the addition of polybrene to the cell culture medium.

HEV does not produce cytopathic effects (CPE) in cell culture so HEV detection is based on PCR. Thus, in some embodiments, detection of HEV at low concentrations is possible by a PCR assay of the present invention. The PCR assay can be used to develop, for example, an infectivity assay for HEV that is precise, accurate and reliable.

The PCR assay originally developed by the National Institutes of Health (NIH) was modified to increase sensitivity. The reverse primer was altered and a completely new probe was designed. Methods using the PCR assay of the present invention consistently scored samples correctly as positive or negative, and are useful in titer calculations. Thus, in a further embodiment, the present invention discloses PCR-based HEV titration assays that comprise the use of polybrene or a culture medium (preferably, cell culture medium) comprising said polybrene.

In one embodiment, the invention relates to a process that involves: propagation of high titer HEV in cell culture by using media supplemented with polybrene; and the detection of HEV by a sensitive PCR assay.

The process can be specific to HEV but the methods for virus propagation can be applied to other non-enveloped viruses. For example, in some embodiments, the present invention was tested with HEV genotype 3 strain Kernow-C1 Passage 6 obtained from the Emerson lab.

It is contemplated that, in some embodiments, the method of producing high-titer HEV mentioned above is carried out in in vitro cultures, preferably in in vitro organ, tissue or cell cultures. In the most preferable embodiment, the method of producing high-titer HEV of the present invention is carried out in an in vitro cell culture.

Both primary cell culture lines and established cell culture lines can be used in the method of the present invention. Cell culture lines used can derive from any organism. For example, the use of insect cells or mammalian cells is contemplated. Preferably, cell culture lines used are derived from pigs (or minipigs) and humans.

Moreover, preferably, cell lines used are derived from liver or kidney. Said liver or kidney from which cell lines derive can be healthy, or diseased, or comprise a malignant or benign growth. In the most preferable embodiment, established cell lines HepG2 (ATCC number HB-8065), or HepG2/C3A (ATCC number CRL-10741) are used.

In some embodiments, the concentration of polybrene is in the range of about 1 µg/ml-about 5 µg/ml. In some embodiments, the concentration of polybrene is about 1, 2, 3, 4 or 5 µg/ml. In a preferred embodiment, the concentration of polybrene is about 4 µg/ml.

The method of the present invention, in some embodiments, yielded HEV titers in the range of about $10^8$ copies/mL-about $10^{10}$ copies/mL. The method of the present invention, in some embodiments, yielded HEV titers in the range of about $10^7$ copies/mL-about $10^{10}$ copies/mL. In a preferred embodiment, the method of the present invention yielded HEV titers of about $10^9$ copies/mL.

In a further embodiment, the present invention refers to a method of producing high-titer HEV comprising the steps of: a) plating cells in culture medium containing polybrene and b) infecting the in vitro culture with HEV. In some embodiments, the cell culture medium from the in vitro cultures is collected to obtain high-titer HEV After step b) above, cultured cells can be collected by any means known in the state of the art (preferably, by trypsinization) and an aliquot may be assayed for the content of HEV. Said content of HEV is preferably determined by PCR, even more preferably with the PCR assay of the present invention and that is described below. See FIG. 5. In alternative embodiments, the content of HEV can be determined by an assay based on immunofluorescence (IF). See FIG. 5.

Moreover, after said step b) cultured cells can be obtained by any means known in the state of the art (preferably, by trypsinization) and HEV stocks can be obtained by any method known in the state of the art. In a preferred embodiment, HEV stock is generated by freeze-thawing cells a number of times, preferably 1 or 2 times. Generated HEV stocks are preferably stored at −65° C. or colder.

It is contemplated that in some embodiments, the method described above also comprises the steps of: c) adding polybrene to the cell culture medium; and d) further passaging the cells infected with HEV.

Steps c) and d) can be repeated, for example, to increase the number of cells producing HEV and to maximize virus spread and infection in the culture. A person skilled in the art can easily determine the number of times that steps c) and d) can be repeated, this is the number of passages that the infected cell line can tolerate on the basis of, for example, the appearance of the cells and their growth curves.

After step d) of each passage, cultured cells can be obtained by any means known in the state of the art (preferably, by trypsinization) and an aliquot may be assayed for the content of HEV. Said content of HEV is preferably determined by PCR, even more preferably with the PCR assay of the present invention and that is described below. See FIG. 5.

Moreover, after said step d) of each passage cultured cells can be obtained by any means known in the state of the art (preferably, by trypsinization) and HEV stocks can be obtained by any method known in the state of the art.

In a preferred embodiment, HEV stock is generated by freeze-thawing cells a number of times, preferably 1 or 2 times. Generated HEV stocks are preferably stored at −65° C. or colder.

Alternatively, medium can also be collected only after the desired or required number of passages have been performed with the infected cell line (this is, after steps c) and d) have been repeated the desired or required number of times).

Step d) of passaging the cells infected with HEV, as a person skilled in the art knows, implies obtaining the cells by any means known in the state of the art. In case cells grow attached to a surface (for example, from a flask or a plate), the cells may need to be detached by any means known in the state of the art, preferably by trypsinization. When enzymes (for example, trypsin) are used to detach cells normally said enzymes need to be inactivated. Usually, in the state of the art, said inactivation is performed by dilution with a solution rich in proteins, preferably with cell culture medium with FBS.

Given the fact that polybrene and culture media comprising said reagent (preferably, cell culture media) allow efficient infection and production of HEV in in vitro cultures (preferably, in vitro cell cultures), they can also be used in HEV titration assays.

Therefore, in a further embodiment, the present invention discloses HEV titration assays are characterized in that they comprise the use of polybrene or a culture medium (preferably, cell culture medium) comprising said polybrene.

The in vitro culture is preferably an in vitro organ, tissue or cell culture. In the most preferable embodiment, the in vitro culture is an in vitro cell culture.

Both primary cell culture lines and established cell culture lines can be used. Cell culture lines used can derive from any organism. For example, the use of insect cells or mammalian cells is contemplated. Preferably, cell culture lines used are derived from pigs (or minipigs) and humans.

Moreover, preferably, cell lines used are derived from liver or kidney. Said liver or kidney from which cell lines derive can be healthy, or diseased, or comprise a malignant or benign growth. In the most preferable embodiment, established cell lines HepG2 (ATCC number HB-8065 or HepG2/C3A (ATCC number CRL-10741) are used.

Preferably, the HEV titration assay of the present invention is a 50% Tissue Culture Infective Dose ($TCID_{50}$) assay that is performed as a person skilled in the art knows, except the presence of virus is indicated by a positive PCR signal and not by viral cytopathology.

In said titration assays, polybrene or the cell culture medium comprising said polybrene are used for the culture of the cells in which HEV samples will be titered.

In another embodiment, a method for the detection of HEV in the HEV stocks is provided.

Said detection can be performed by any method or means known in the state of the art. Nevertheless, in a preferred embodiment, detection is performed by PCR.

In a preferred embodiment, PCR used for the detection of HEV is real time reverse transcriptase PCR that comprises a first step of reverse transcription of viral RNA to complementary DNA (cDNA), and a second step of real time PCR that is preferably performed using a double quenched probe.

Figure 4:
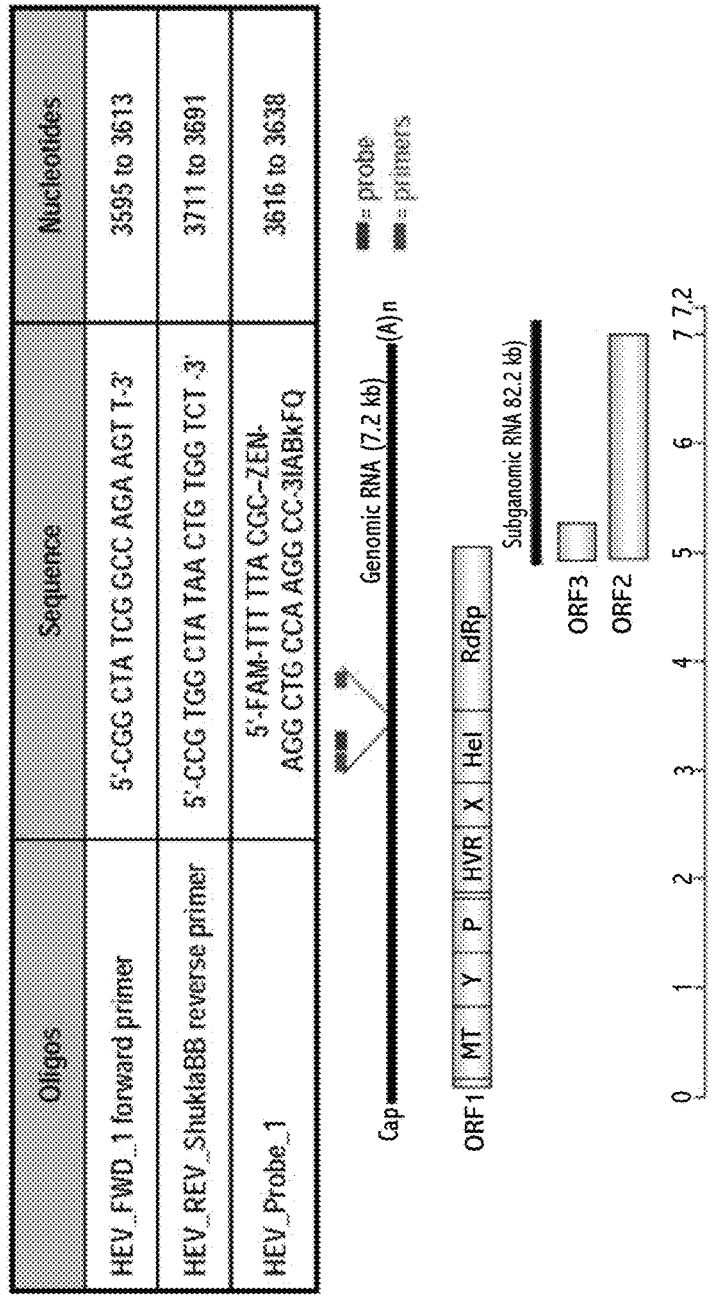
FIG. 4 shows the nucleotide sequences of primers and probes used for HEV PCR assay and their location on the HEV genome according to some embodiments of the disclosure herein.

In the most preferred embodiment, in the second step, the following oligonucleotides are used as primers and probe (FIG. 4):

a) forward primer:
(SEQ ID NO: 1)
5'-CGGCTATCGGCCAGAAGTT-3' b) reverse primer:
(SEQ ID NO: 2)
5'-CCGTGGCTATAACTGTGGTCT-3' c) probe:
(SEQ ID NO: 3)
5'-FAM-TTTTTACGC-ZEN-AGGCTGCCAAGGCC-3IABkFQ-3'

Data from studies to assess the performance of the HEV PCR-based infectivity assay is summarized in Table 2.

TABLE 2

Assessment of HEV PCR-based Infectivity Assay Performance

| Assay Parameter | Method Description | Acceptance Criteria | Results | |
|---|---|---|---|---|
| Precision - Repeatability | Multiple measurements of single sample by one analyst in one day | CV ≤ 30% | High: Med: Low: | Pass |

TABLE 2-continued

Assessment of HEV PCR-based Infectivity Assay Performance

| Assay Parameter | Method Description | Acceptance Criteria | Results | |
|---|---|---|---|---|
| Precision - Intermediate | Multiple measurements of single sample by multiple analysts over several days | p-value > 0.01 or difference in mean titers < 0.5 log$_{10}$ | High: P 0.4 Med: Diff mean titer p 0.4 Low: P 0.6 | Pass |
| Accuracy | Measures closeness of results to expected titers | CV ≤ 30% Nominal 50-150% | CV: 2-17% Nom: 105-136% | Pass |
| Linearity | Measures relationship of assay results to actual virus concentration | R$^2$ for regression line > 0.95 | R$^2$ = 0.99 | Pass |
| Limit of Quantitation | Lowest conc. of virus detected with acceptable precision, & accuracy | Lowest concentration with CV ≤ 30% | 10$^{0.8}$ TCID$_{50}$/mL | Pass |
| Range | Interval where virus is detected with acceptable precision, accuracy, & linearity | CV ≤ 30% | 10$^{0.8}$ to 10$^{6.4}$ TCID$_{50}$/mL | Pass |
| Detection Limit - Standard Titration | Lowest concentration of virus that can be detected | Lowest concentration with CV ≤ 50% | 10$^{0.8}$ TCID$_{50}$/mL | Pass |
| Detection Limit - Large Volume Titration | Titrated 12.6 mL of 10$^{6.4}$ TCID$_{50}$/mL stock after 10$^{6.6}$-fold dilution | Expected value: 0-2 positive/252 wells | 2 positive/252 wells = 10$^{-0.5}$ TCID$_{50}$/mL | NA |

In a preferred embodiment cells are titrated in 96 well-plate and HEV RNA extracted with magnetic Bioclone beads or magnetic Dynabeads, more preferably Dynabeads are used.

For a better understanding, certain embodiments of the present invention are described in more detail with reference to the accompanying figures, which are presented by way of example, and with reference to illustrative examples which are not a limitation of the present invention.

EXAMPLES

Example 1

Cell Growth Patterns of HepG2/C3A Cells in Different Growth Media

Figure 1B:
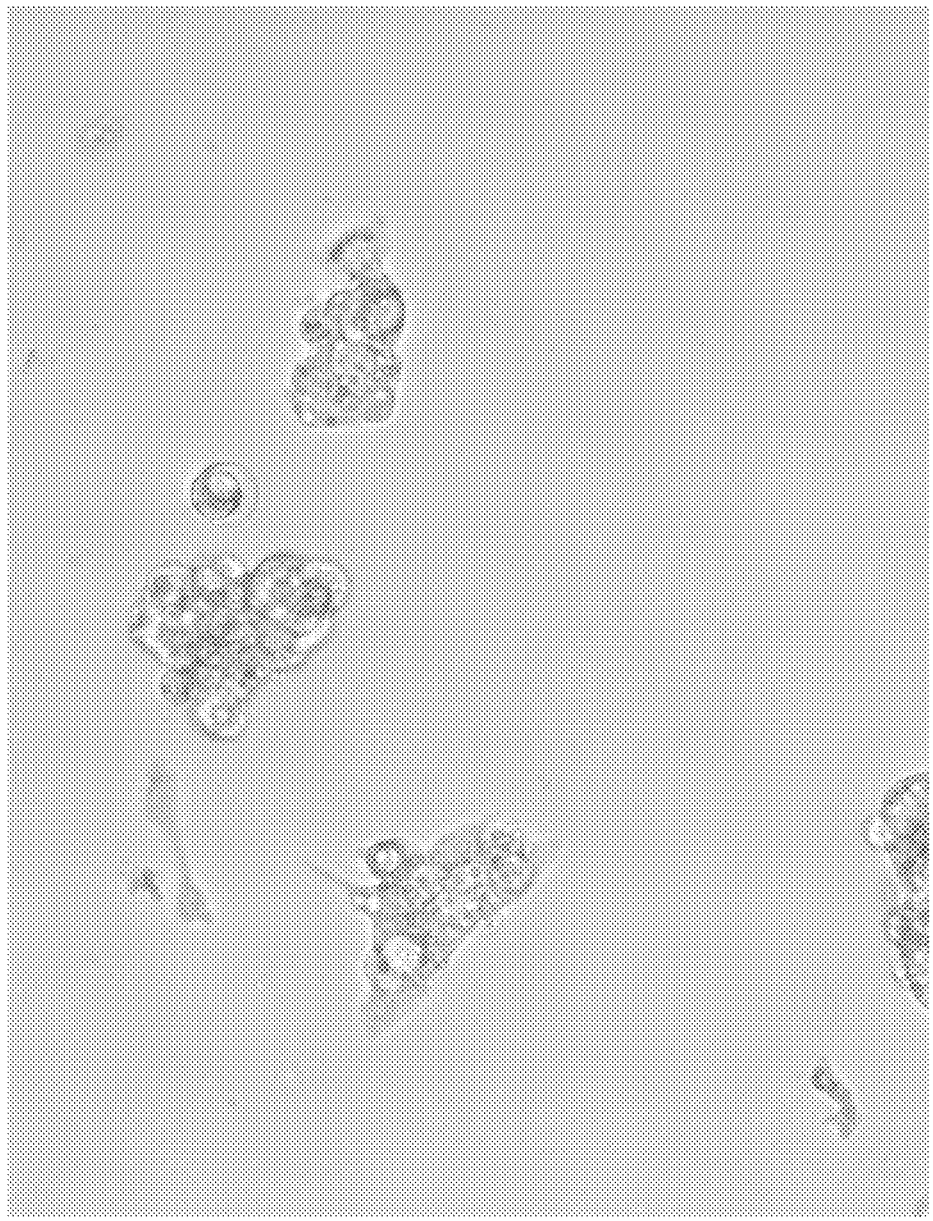
Figure 1C:
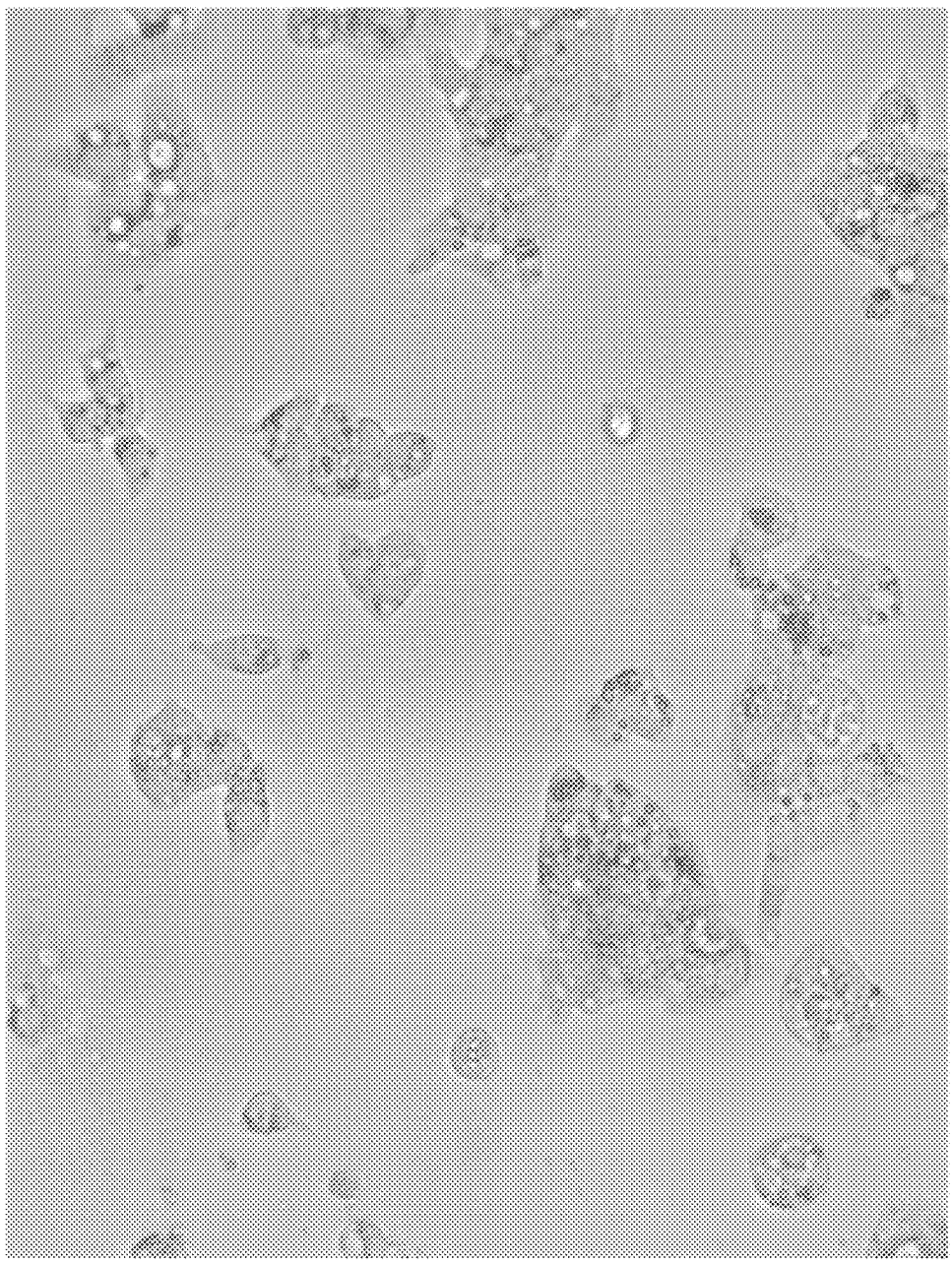

HepG2/C3A (10$^6$) cells were seeded in 25 cm$^2$ flasks and cultured in one of the following cell culture media:
DMEM+10% FBS+NHG (Non-essential amino acids, fungizone, HEPES, gentamicin);
DMEM+10% FBS+NHG+1 mM pyruvate; or
DMEM+10% FBS+NHG+1 mM pyruvate+4 ug/mL polybrene.
Images, taken at 20× magnification after 1 day, are shown in FIG. 1. HepG2/C3A cells cultured in medium DMEM+10% FBS+NHG (A) or DMEM+10% FBS+NHG+pyruvate (B) grew in clumps, which would make infection with virus (e.g. HEV) very difficult. On the other hand, when HepG2/C3A cells were cultured in DMEM+10% FBS+NHG+pyruvate+polybrene (C), cells attached and grew in a flat even monolayer, which should be easily infected by a virus (e.g. HEV).

Figure 2A:
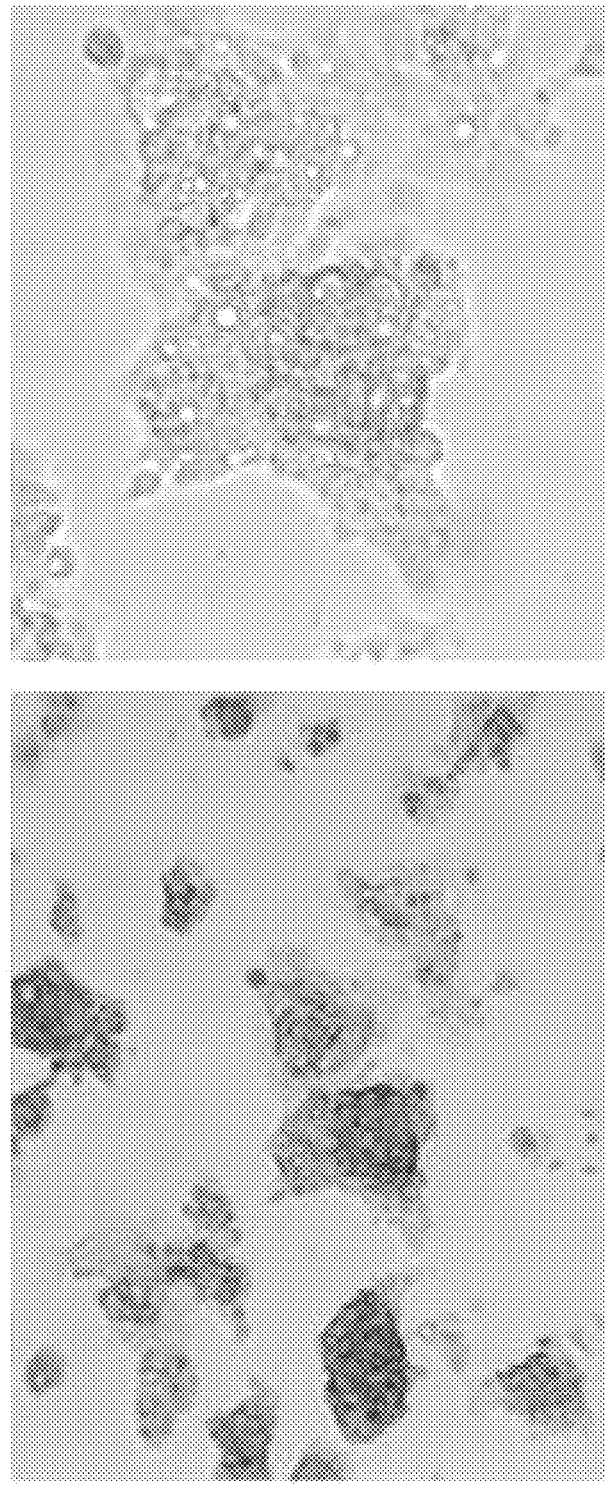
FIG. 2A-FIG. 2C show images taken at 10× magnification (left) or 20× magnification (right) of HepG2/C3A cells cultured for 3 days.
Figure 2B:
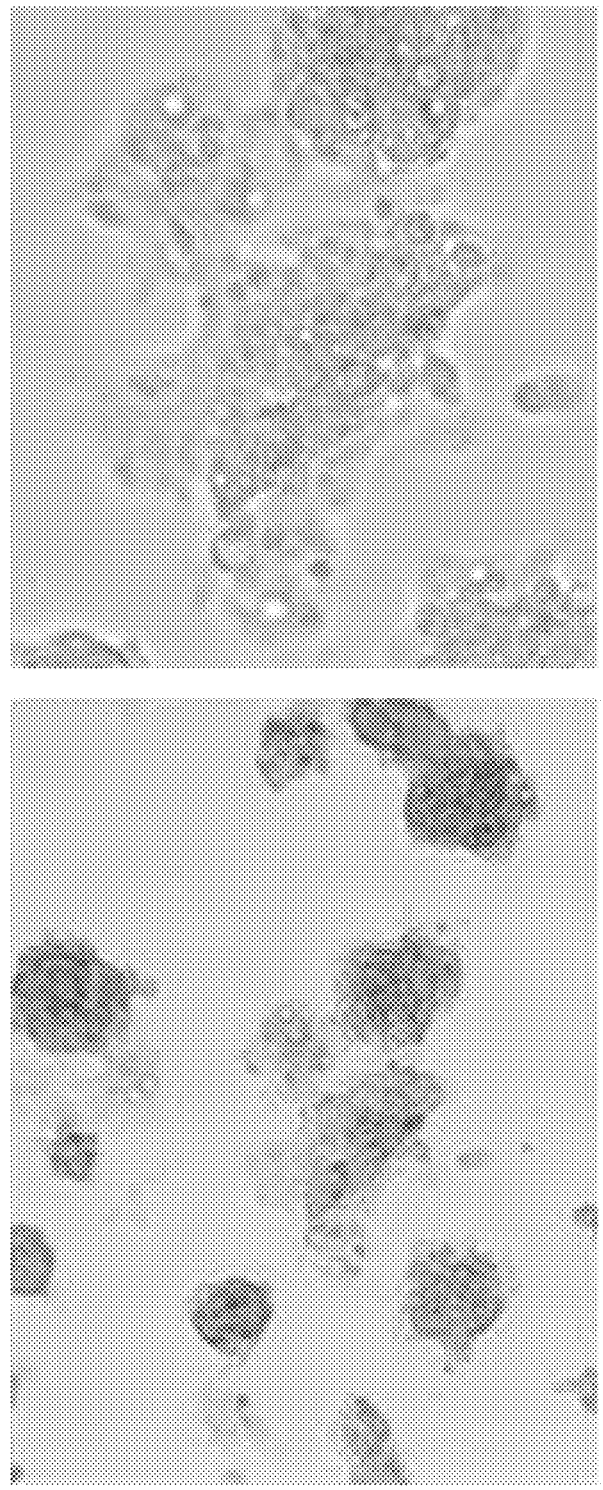
Figure 2C:
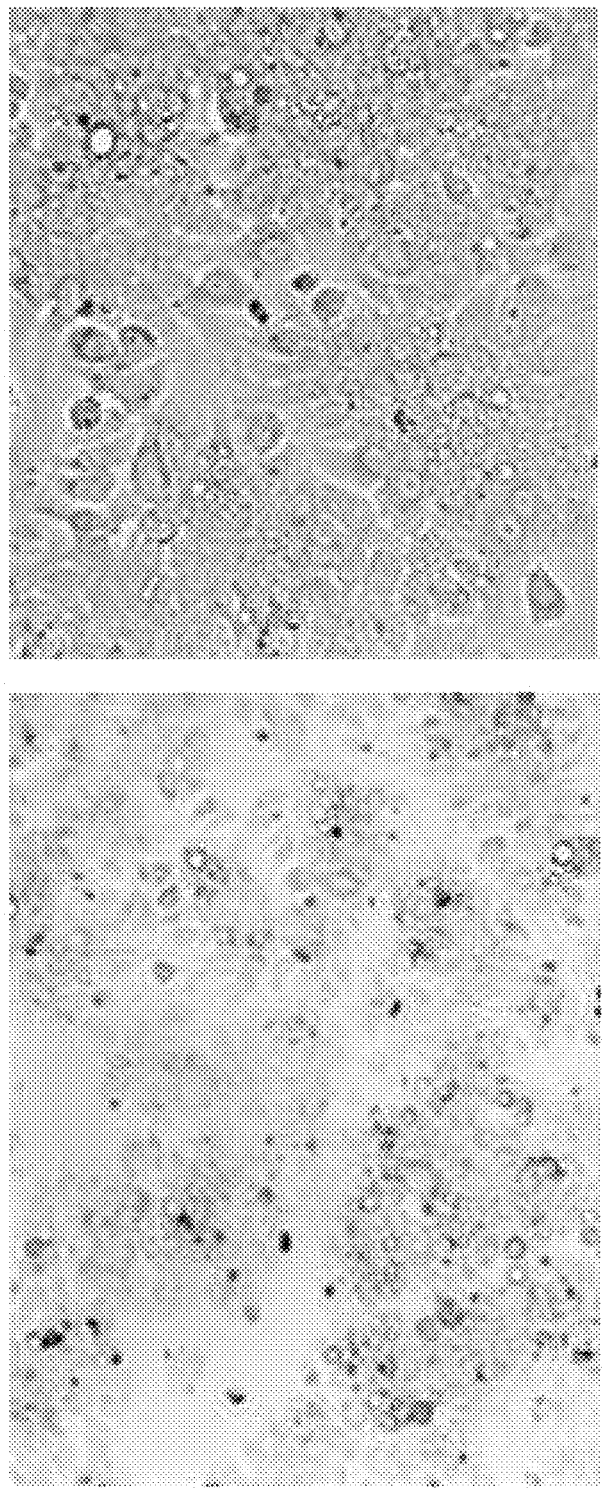
Figure 3:
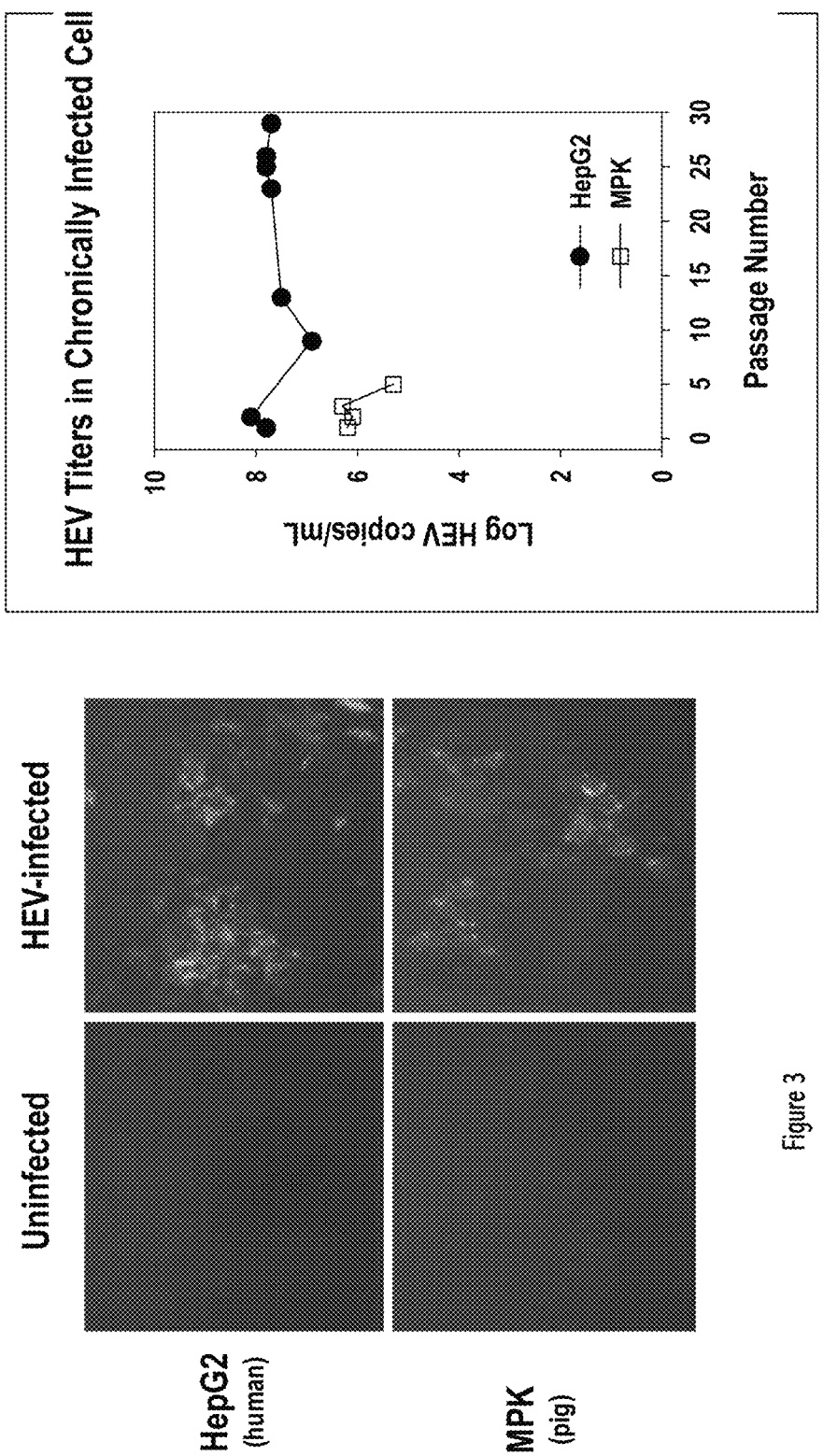
FIG. 3 shows a comparison of HEV RNA titers in chronically infected HepG2 (human) to MPK (pig) cells assessed by HEV PCR assay according to some embodiments of the disclosure herein. Polybrene was not used for MPK cells because MPK cell attachment to plating surfaces is very efficient.

Images, taken at 10× and 20× magnification after 3 days, are shown in FIG. 2. Similar to the 1 day cells, HepG2/C3A cells cultured in DMEM+10% FBS+NHG (A) or DMEM+10% FBS+NHG+pyruvate (B) grew in clumps but cells grown in DMEM+10% FBS+NHG+pyruvate+polybrene (C) grew in a flat even monolayer. Since cell clumps would impede uniform infection by viruses, the efficiency of HEV infection would most likely be higher in cell grown in the presence of polybrene.

Example 2

Establishment of HEV-infected Cells

Cell culture flasks were seeded for infection as follows: HepG2 or HepG2/C3A cells were trypsinized according to protocols or procedures known in the state of the art. Ten mL of Growth Medium (base medium in accordance with the requirements of the cell line used plus polybrene at a concentration of about 1-about 5 μg/mL) were added to neutralize the trypsin and the suspension was pipetted up and down to break up cell clumps. The cells were then seeded at a density of approximately 10$^6$ cells per 150 cm$^2$ flask and left overnight in a 37° C. incubator.

Cells were infected with HEV by removing the medium from the flask and adding HEV Stock (clarified virus-infected cell lysate) at a Multiplicity of Infection (MCI) of 0.1-1.0 and in a total volume of 5-10 mL. The cells were incubated at 37° C. for at least 1 hour, during which time, the flask was periodically rocked back and forth to prevent cells from drying out and to distribute the virus inoculum evenly across cells. Additional Growth Medium (10-20 mL per flask) was added and the flask was kept at 37° C. until the cell monolayer was confluent (approximately 1 week).

Example 3

Propagation of HEV-infected Cells

Infected cells (HepG2 or HepG2/C3A) in a 150 cm$^2$ flask were trypsinized in accordance with Example 1 when the cell monolayer became confluent. If multiple flasks were trypsinized, cell suspensions were pooled together before proceeding.

An aliquot, no less than 1 mL, of the trypsinized cell suspension was taken to analyze for HEV RNA by PCR. The remaining cell suspension was discarded or divided into other 150 cm$^2$ flasks at a density equivalent to the number of cells in 1/6th of a confluent monolayer (1:6 split). Growth Medium was added to bring the final volume in each 150 cm$^2$ flask to 20-25 mL and the flasks were incubated until the cells reached confluency (approximately 1 week).

This procedure was repeated each week until the quantity of HEV RNA in the 1 mL sample, that had been removed for PCR analysis, reached high titers. In some embodiments, high titer was in the range of about 10$^8$ copies/mL-about 10$^{10}$ copies/mL. In some embodiments, high titer was in the range of about 10$^7$ copies/mL-about 10$^{10}$ copies/mL. Some flasks were then trypsinized and split for continued passage of the HEV-infected cells while the remaining flasks were processed as HEV stock.

Flasks of HEV stock were frozen and thawed 1-2 times to rupture infected cells and release virus. The infected lysates were then pooled, aliquoted into appropriate containers and stored at no warmer than −65° C.

Example 4

HEV PCR-based infectivity Assay

HEV titration in a 96-well plate format is described in this example but the assay could be easily adapted to multiwell plates of other sizes.

Serial dilutions of a HEV stock were made and added to wells seeded with HepG2 or HepG2/C3A cells. Virus was allowed to adsorb for no less than 1 hr at 37° C. and Growth Media was added. Plates were incubated at 37° C. for no less than 2 days before aspirating the media from the wells and washing/aspirating the cells no less than 2× with buffer (e.g. PBS). The plates were then extracted for PCR or were stored at no warmer than −65° C. until ready for extraction.

The Dynabeads® mRNA DIRECT' Micro Kit (Life Technologies) was used to extract polyadenylated RNA (e.g. HEV RNA) from cells in each well of the titration plate, following manufacturer instructions. The resulting eluate (poly A RNA) was immediately processed for PCR amplification or stored at no warmer than −65° C. until ready for PCR amplification.

One step RT-PCR was used to detect HEV RNA in samples, using the primers and probes as previously discussed. The assay conditions for each reaction were as follows:
 a) Reagents; 5.0 µl 4× TaqMan® Fast Virus 1-Step Master Mix (Life Technologies), 0.08 µL 100 mM primer F+R, 0.04 µL 100 mM probe, 0.4 µL SUPERase In (Life Technologies), 4.4 µL water and 10 µL template (total 20 µl)
 b) Reaction: 52° C. 10 minutes, 95° C. 30 seconds, and 40 cycles of 95° C. 15 seconds, 56° C. 45 seconds, PCR and cycle threshold (Ct) value determination were performed using an AB 7500 Real Time PCR System (Applied Biosystems, Foster City, Calif.) and accompanying software according to manufacturer's instruction.

PCR was quantitative or qualitative. For quantitative PCR, a HEV cDNA plasmid obtained from the NIH was linearized with MluI and transcribed using the mMESSAGE mMACHINE® Kit (Life Technologies) to generate 7.2 kb RNA transcripts with a 7-methyl guanosine cap and poly A tail. The transcripts were purified with the Ambion Mega-Clear kit (Life Technologies), quantified with the Quant-iT™ RiboGreen® RNA Reagent and Kit (Invitrogen) and used as standards to construct RNA standard calibration curves.

RNA standard curves were generated by the AB7500 software system by plotting the Ct values against the logarithm of the calculated copy numbers for the standards.

Figure 5:
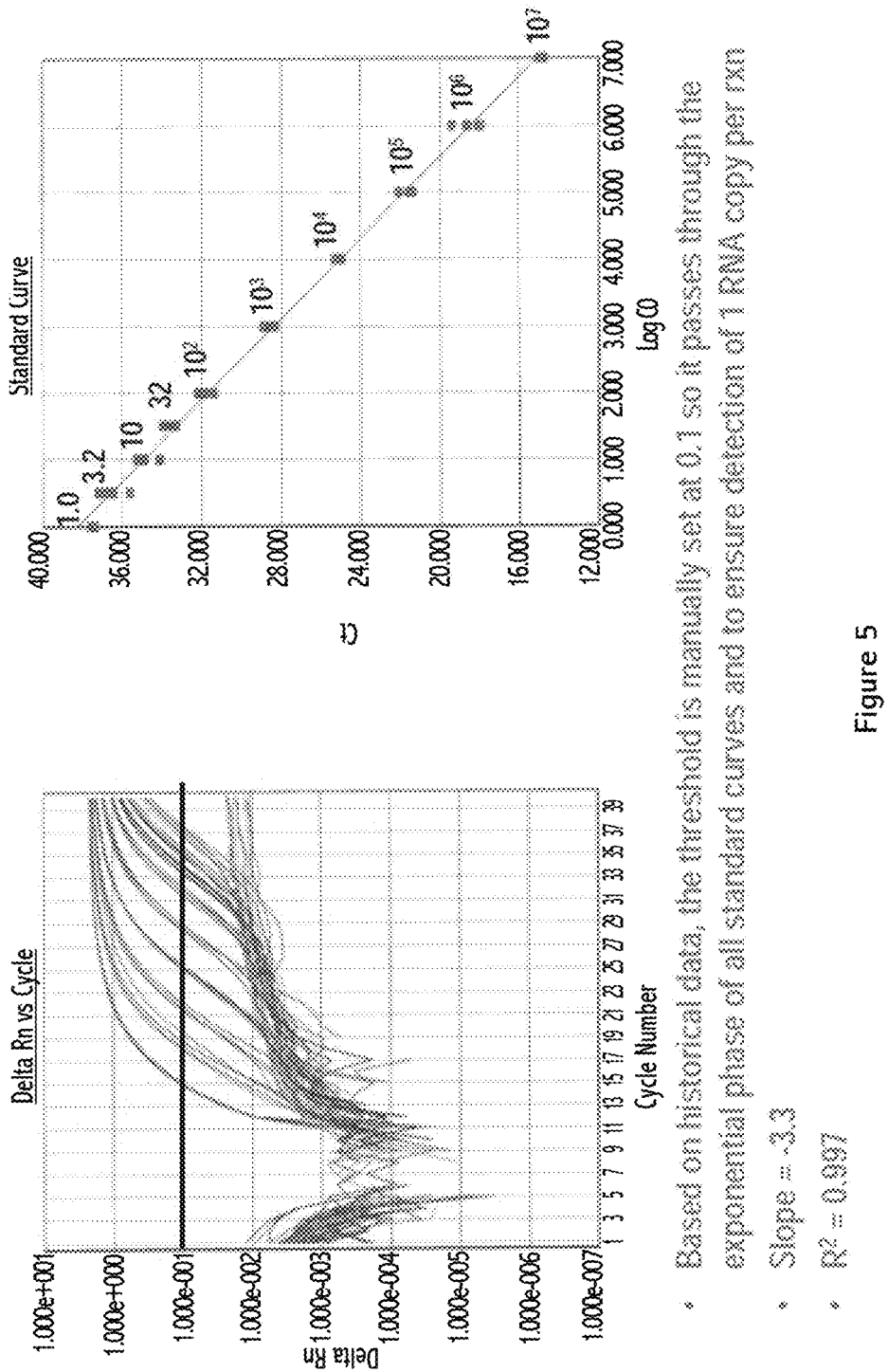
FIG. 5 shows the standard curve for HEV PCR assay according to some embodiments of the disclosure herein.

FIG. 5 (right panel) shows a typical standard curve. All curves had a wide dynamic range, ranging from $10^0$ to $10^7$ copies per reaction, and were linear with a correlation coefficient of $r^2 > 0.99$. The percent efficiency of amplifications was calculated as % E=[10 (−1/slope)−1]*100. Based on n=22 HEV qPCR standard curves, the efficiency of HEV quantitative PCR was 100.4% (data not shown).

For qualitative PCR, wells were scored positive or negative based on the presence of a positive PCR signal. Virus titers were calculated as $TCID_{50}/mL$ using the appropriate statistical methods: Spearman-Kärber, MPN or Poisson.

Example 5

Assessment of HEV PCR-based Infectivity Assay Performance

Assay qualification studies were performed to assess the operational characteristics of the HEV infectivity assay. The parameters evaluated were precision, accuracy, linearity, limit of quantitation and detection, and dynamic range.

Acceptance criteria were the same as those typically used for other virus titration assays.

The results are summarized in Table 2 and show that the assay passed all tests.

DEFINITIONS

HepG2: Hepatocellular carcinoma cells obtained from the American Type Culture Collection (ATCC number HB-8065)

MPK: Minipig kidney cells obtained from the American Type Culture Collection (ATCC number CCL-66)

DMEM: Dulbecco's Modified Eagle Medium

FBS: Fetal Bovine Serum

HEPES: N-2-hydroxyethylpiperazine-N'-2-ethanesulfonic acid

NEAA: Nonessential Amino Acids

NHG: A mixture of the following: Nonessential Amino Acids, Fungizone, HEPES, and Gentamicin Titration: The process of serially diluting a sample to bracket an expected viral titer and transferring the diluted sample to a plate to determine the $TCID_{50}/mL$ Titer: Concentration of a substance (virus) in solution or the strength of such a substance determined by titration SK: Spearman-Karber is a statistical method to calculate virus titers in samples with relatively high concentrations of virus. This method is used when the proportion of positive wells at any dilution is >25%

MPN: Most Probable Number is a statistical method to calculate virus titers in samples with relatively low concentrations of virus. MPN is used when the proportion of positives wells at all dilutions is <25%.

Poisson: Poisson is a statistical method to calculate virus titers in samples with extremely low concentrations of virus. This method is used when no positive wells are observed.

ATCC: American Type Culture Collection $TCID_{50}$: Corresponds to 50% Tissue Culture Infective Dose (Endpoint dilution assay). It is a measurement of infectious virus titer that quantifies the amount of virus required to kill 50% of infected hosts or to produce cytopathic effect in 50% of inoculated tissue culture cells.

REFERENCES

1. Okamoto H (2011) Hepatitis E virus cell culture models. Virus Research 161: 65-77.
2. Tanaka T, et al (2007) Development and evaluation of an efficient cell-culture system for Hepatitis E virus. J Gen Virol 88: 903-911.
3. Tanaka T, et al (2009) Development and Characterization of a Genotype 4 Hepatitis E Virus Cell Culture System Using a HE-JF5/15F Strain Recovered from a Fulminant Hepatitis Patient. J Clin Microbiol 47: 1906-1910.
4. Shukla P, et al (2011) Cross-species infections of cultured cells by hepatitis E virus and discovery of an infectious virus-host recombinant. PNAS. 108 (6): 2438-2443.
5. Shukla P, et al (2012) Adaptation of a Genotype 3 Hepatitis E Virus to Efficient Growth in Cell Culture Depends on an Inserted Human Gene Segment Acquired by Recombination. J Virol 86 (10): 5697-5707
6. U.S. Provisional Patent Application No. 61/431,377
7. U.S. Provisional Patent Application No. 61/554,323
8. U.S. patent application Ser. No. 13/978,839
9. International PCT Application No. PCT/US2012/020830

What is claimed is:

1. A method of producing a titer of Hepatitis E Virus (HEV), the method comprising:
 a) culturing a cell line in vitro in a medium comprising a concentration of polybrene, and b) infecting the cell line with HEV, wherein the cell line is HepG2 (ATCC number HB-8065) or HepG2/C3A (ATCC number CRL-10741), wherein the concentration of polybrene is about 1 μg/ml - about 5 μg/ml.

2. The method according to claim 1, wherein the titer of HEV is about $10^8$ copies/mL - about $10^{10}$ copies/mL.

3. The method according to claim 1, wherein the titer of HEV is about $10^7$ copies/mL - about $10^{10}$ copies/mL.

4. The method according to claim 1, wherein the method further comprises the steps of:

a) adding a concentration of polybrene to the medium;

b) passaging the HEV-infected cell line in the medium comprising polybrene; and c) collecting the medium and/or infected cells.

5. The method according to claim 4, wherein the titer of HEV obtained in the medium and/or infected cells is about $10^8$ copies/mL - about $\mathbf{10}^{10}$ copies/mL.

6. The method according to claim 4, wherein the titer of HEV obtained in the medium and/or infected cells is about $\mathbf{10}^7$ copies/mL - about $\mathbf{10}^{10}$ copies/mL.

7. A method of determining a presence and/or a level of HEV in a sample, the method comprising the steps of:

a) providing the sample to a mixture comprising a cell line and a culture medium, wherein the culture medium comprises polybrene;

b) incubating the mixture comprising the sample from step a), to allow for the propagation of HEV, if present in the sample;

c) collecting a portion of step b), the portion comprising HEV, if present and propagated during step b); and d) measuring the presence and/or the level of a biological substance associated with HEV in the collected portion.

8. The method according to claim 7, wherein the cell line is selected from the group consisting of HepG2 (ATCC number HB-8065) and HepG2/C3A (ATCC number CRL-10741).

9. The method according to claim 7, wherein the biological substance comprises a polynucleotide and/or a polypeptide sequence of HEV.

10. The method according to claim 7, wherein measuring the presence and/or the level of a biological substance comprises the steps of:
  a) providing a first reaction mixture by mixing the collected portion with a first solution so as to expose a polynucleotide of HEV, if HEV is present in the collected portion, wherein the polynucleotide is an RNA of HEV;
  b) providing a second reaction mixture by adding, to the first reaction mixture, a first reagent so as to produce a complementary deoxyribonucleic acid (cDNA) that is at least partially complementary to the RNA of HEV;
  c) providing a third reaction mixture by adding, to the second reaction mixture, a second reagent comprising a pair of polynucleotides to amplify a sequence of the cDNA that is at least partially complementary to each of the pair of polynucleotides;
  d) providing a fourth reaction mixture by amplifying the sequence; and
  e) determining a concentration of the amplified sequence in the fourth reaction mixture.

11. The method according to claim 10, wherein said determining the concentration comprises:
  a) providing the fourth reaction mixture;
  b) providing a one or more controls comprising a predetermined amount of the cDNA of HEV;
  c) adding an agent to the fourth reaction mixture and the one or more controls, wherein said agent is at least partially specific to the amplified sequence in the fourth reaction mixture and the predetermined amount of the cDNA of HEV in the one or more controls; and
  d) calculating a level of recognition of HEV by the agent in the fourth reaction mixture relative to the one or more controls.

12. The method according to claim 10, wherein said pair of polynucleotides comprises:

a)
  (SEQ ID NO: 1)
  5'-CGGCTATCGGCCAGAAGTT-3'
  b)
  (SEQ ID NO: 2)
  5'-CCGTGGCTATAACTGTGGTCT-3'.

13. The method according to claim 11, wherein the agent comprises:

(SEQ ID NO: 3)
  5'-FAM-TTTTTACGC-ZEN-AGGCTGCCAAGGCC-3IABkFQ-3'.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic; HEV derived primer

<400> SEQUENCE: 1
cggctatcgg ccagaagtt                                                    19

<210> SEQ ID NO 2
<211> LENGTH: 21
<212> TYPE: DNA
<213> ORGANISM: Artificial Sequence
<220> FEATURE:
<223> OTHER INFORMATION: Synthetic; HEV reverse primer

<400> SEQUENCE: 2
ccgtggctat aactgtggtc t                                                 21

<210> SEQ ID NO 3
<211> LENGTH: 23
<212> TYPE: DNA
<213> ORGANISM: Artificial Sequence
<220> FEATURE:
<223> OTHER INFORMATION: Synthetic; HEV Probe
<220> FEATURE:
<221> NAME/KEY: misc_binding
<222> LOCATION: (1)..(1)
<223> OTHER INFORMATION: FAM at the 5' end
<220> FEATURE:
<221> NAME/KEY: misc_binding
<222> LOCATION: (9)..(10)
<223> OTHER INFORMATION: ZEN between nucleotides 9 and 10
<220> FEATURE:
<221> NAME/KEY: misc_binding
<222> LOCATION: (23)..(23)
<223> OTHER INFORMATION: 3IABkFQ at the 3' end

<400> SEQUENCE: 3
tttttacgca ggctgccaag gcc                                               23